United States Patent [19]

Kimura et al.

[11] Patent Number: 4,647,202

[45] Date of Patent: Mar. 3, 1987

[54] SPECTROPHOSPHORIMETRY

[75] Inventors: Mitsuyoshi Kimura; Taro Nogami; Minoru Owada; Hiroyuki Koshi, all of Katsuta, Japan

[73] Assignee: Hitachi, Ltd., Tokyo, Japan

[21] Appl. No.: 687,915

[22] Filed: Dec. 31, 1984

[30] Foreign Application Priority Data

Dec. 29, 1983 [JP] Japan .................. 58-245869

[51] Int. Cl.$^4$ ........................................... G01N 21/64
[52] U.S. Cl. ................................. 356/318; 250/458.1
[58] Field of Search ............... 356/317, 318, 328, 334; 250/458.1, 459.1, 461.1, 461.2

[56] References Cited

U.S. PATENT DOCUMENTS 3,092,722  6/1963  Howerton ................... 250/461.1 X
3,532,429 10/1970  Hughes et al. ..................... 356/320
4,299,486 11/1981  Nogami et al. ..................... 356/318

Primary Examiner—Vincent P. McGraw
Attorney, Agent, or Firm—Antonelli, Terry & Wands

[57] ABSTRACT

A spectrophosphorimeter with a single spectrometer so as to obviate the need of a couple of spectrometers of conventional spectrophosphorimeters, wherein one spectrometer is operated as an excitation-side spectrometer only when the light is allowed to pass a light interceptor, and the other spectrometer works as a phosphorescence-side spectrometer only when the light is substantially interrupted. The single spectrometer is used on the excitation side when the light is allowed to pass and on the phosphorescence side when the light is interrupted.

10 Claims, 8 Drawing Figures

SPECTROPHOSPHORIMETRY

BACKGROUND OF THE INVENTION

The present invention relates to a spectrophosphorimeter, or more in particular to a spectrophosphorimeter which can be suitably reduced in size and improved in sensitivity.

The spectrophosphorimetry is a method of measuring the phosphorescence produced from a sample irradiated with an excitation light, and has the advantage of a higher sensitivity than the spectrofluorimetry.

A spectrophosphorimeter comprises a light intercepter between a light source and a spectrometer on an excitation side of the spectrofluorimeter as disclosed in U.S. Pat. No. 4,299,486.

A conventional spectrophosphorimeter requires a couple of spectrometers; one is an excitation-side spectrometer for taking a spectrum of the light from a light source and irradiating the excitation light on a sample, and the other is a phosphorescence-side spectrometer for taking a spectrum of the phosphorescence emitted from the sample, and has the disadvantage of a complicated construction and bulkiness.

SUMMARY OF THE INVENTION

The object of the present invention is to provide a spectrophosphorimeter which is capable of spectrophosphorimetry with a single spectrometer and is thus simple in construction and small in size.

In the spectrophosphorimeter, the excitation light is irradiated on a sample only when the light is allowed to pass an intercepter. The phosphorescence from the sample, on the other hand, continues to be emitted even while the light is blocked by the light interceptor. When the light is allowed to pass, however, the dispersed light from the sample caused by the excitation light is superimposed on the phosphorescence. As a result, the phosphorescence emitted from the sample while the light interceptor is working is the only light that can be utilized.

The inconvenience of the conventional spectrophosphorimeter in which the excitation-side spectrometer is used only when the light interceptor allows the light to pass, while the phosphorescence-side spectrometer is operated only when the light is substantially blocked, is obviated by the present invention comprising a single spectrometer which is used as an excitation-side spectrometer when the light is passed by the light interceptor and acts as a phosphorescence-side spectrometer when the light is blocked by the light interceptor.

As a result, phosphorescence can be measured with a single spectrometer, thereby simplifying the construction and reducing the size of the spectrophosphorimeter.

DESCRIPTION OF THE PREFERRED EMBODIMENT

Figure 1:
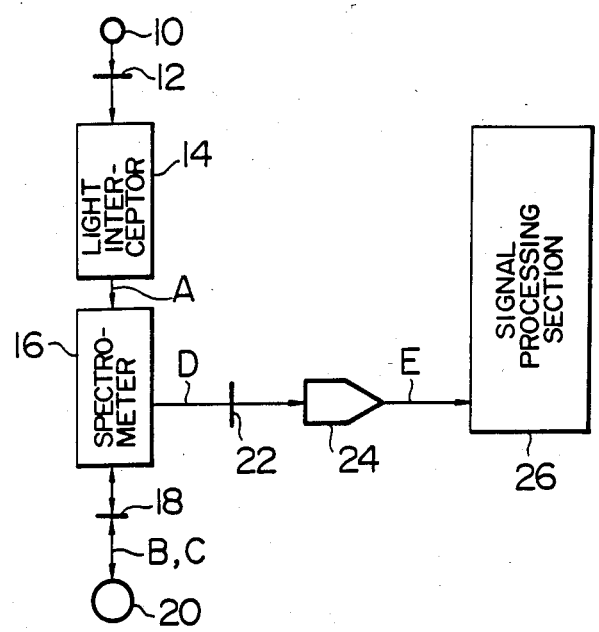
FIG. 1 is a diagram showing a configuration of a spectrophosphorimeter according to an embodiment of the present invention.

In FIG. 1, the light emitted from a light source 10 is converged by a light convergence section 12, and the light A thus converged is introduced to a spectrometer 16 intermittently through a light interceptor 14. A spectrum of light of a predetermined wavelength that has been picked up by the spectrometer 16 is irradiated on a sample 20 through a converging section 18 as an excitation light B. After the sample 20 is excited for a predetermined period of time, the light from the light source 10 is interrupted by the light interceptor 14, while the spectrometer 16 is switched to the use for phosphorescence at the same time. The phosphorescence C that is emitted from the sample 20, which is attributable to the irradiation of the excitation light B, is introduced to spectrometer 16 through the light convergence section 18 only during the period when the light interceptor 14 is working to intercept the light. The phosphorescence C introduced to the spectrometer 16 is reduced to a spectrum, so that the light D of a predetermined wavelength is applied through a light convergence section 22 to a detector, where it is converted into an electrical signal E. This electrical signal E is applied to and processed at a signal processing section 26.

Figure 2:
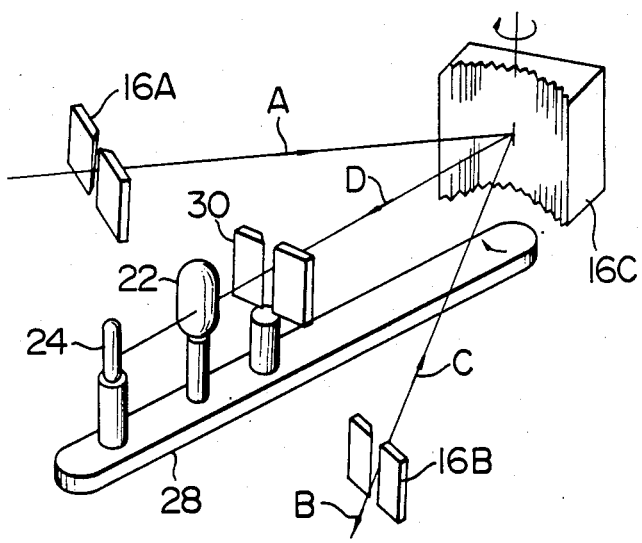
FIGS. 2 to 4 are diagrams showing different embodiments of the spectrometer in detail.

FIG. 2 shows the spectrometer 16 in detail. A slit 16A on light source side and a slit 16B on sample side are fixed on the Rowland circle, and the wavelength of the excitation light B is set by rotation of a concave diffraction grating 16C. The wavelength of the phosphorescence C, on the other hand, is set by rotating an arm 28 around the concave diffraction grating 16C. The arm 28 has arranged thereon a detection-side slit 30, a convergence section 22 and a detector 24. The detection-side slit 30 is arranged from the center of the concave diffraction grating 16C at a distance equal to the diameter of the Rowland circle. The phosphorescence component of the spectrum diffracted by the concave diffraction grating 16C is converted at the detection-side slit 30.

Now, the relation between the concave diffraction grating 16C and the arm 28 will be explained. From the standpoint of entry of the light from the sample-side slit 16B, the arm 28 is always required to be located on the long-wavelength side of the excitation wavelength. With the rotation of the concave diffraction grating 16C, therefore, the arm 28 is adapted to rotate by the same rotational angle, whereas the arm 28 is locked not to move toward the short wavelength side of the excitation wavelength. In this way, the arm 28 is allowed to rotate toward the long wavelength side of the excitation wave, thus making the spectrophosphorimetry possible. If a spectrometer shown in FIG. 2 is used, the excitation wavelength and the phosphorescence wavelength can be selected as desired with a simple configuration and small size of the spectrophosphorimeter.

Figure 3:
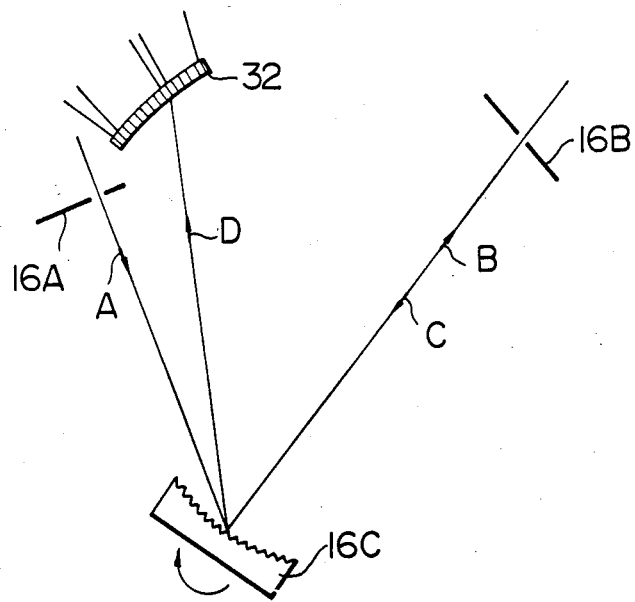

Another embodiment of the spectrometer is shown in FIG. 3. A slit 16A on light source side, a sample-side slit 16B and a detector array 32 are arranged on the Rowland circle, and the wavelength of the excitation light B irradiated on the sample is selected by rotating the concave diffraction grating 16C. The phosphorescence C emitted from the sample is diffracted at the concave diffraction grating 16C and converged on the detector array 32, so that it is possible to obtain a spectral distribution at a time. The wavelength associated with each element of the detector array 32 changes with the rotation of the concave diffraction grating 16C, and the processing according to the change is performed at a signal processing section. The use of the spectrometer shown in FIG. 3 realizes a spectrophosphorimeter of high-speed light-metering ability.

Figure 4:
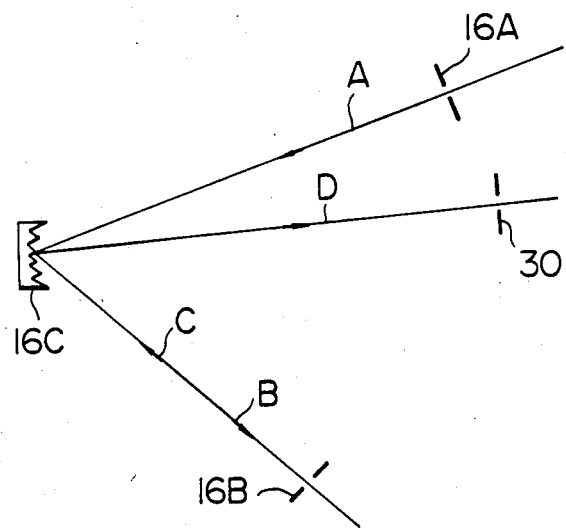

FIG. 4 shows still another spectrometer. A concave diffraction grating 16C, a slit 16A on light source side, a detection-side slit 30 and a sample-side slit 16B are fixedly disposed on the Rowland circle. Assuming that the phosphorescence centers the system from the sample-side slit 16B, the detection-side slit 30 is arranged on the long wavelength side of the light irradiated on the sample. The spectrometer of this construction is used suitably as a spectrophosphorimeter and is very simple in configuration.

Figure 5A:
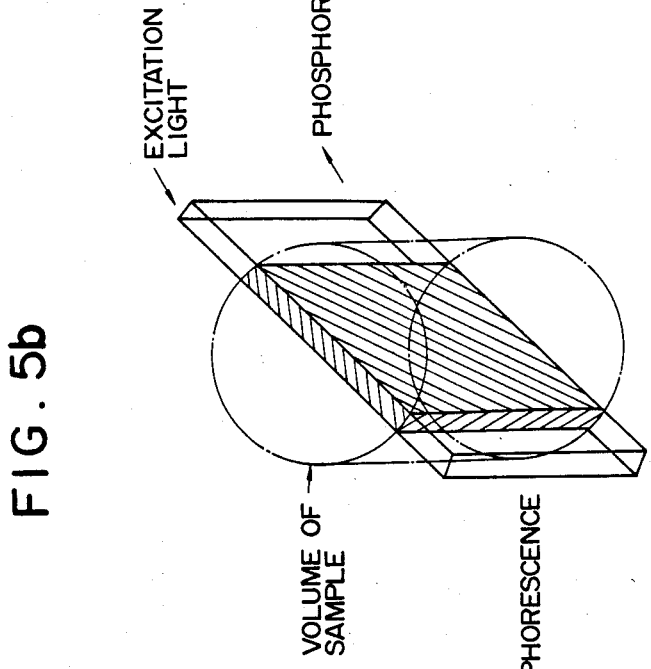
FIGS. 5a and 5b are diagrams for explaining the light-measuring sensitivity.
Figure 5B:
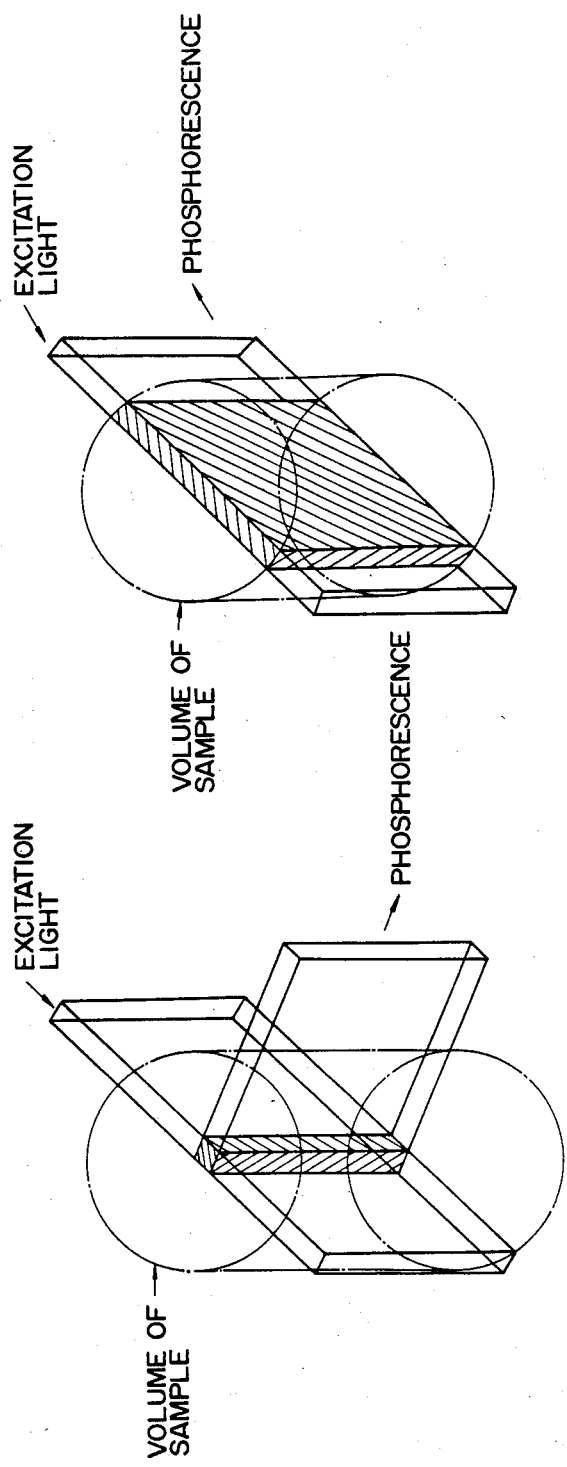

FIGS. 5a and 5b are for explaining the light-metering sensitivity, in which FIG. 5a shows the prior art and FIG. 5b the present invention. Conventionally, a couple of spectrometers are used so that the optical axis of the excitation light is crossed with that of the phosphorescence convergence section as shown in FIG. 5a, with the result that it is possible to use the phosphorescence derived only from part of the volume (hatched in the drawing) of the sample irradiated with the excitation light. According to an embodiment of the present invention shown in FIG. 1, by contrast, the optical axis of the excitation light coincides with that of the phosphorescence convergence section as shown in FIG. 5b, and therefore the whole volume (hatched in the drawing) irradiated with the excitation light can be used, resulting in an improved phosphorescence recovery and a higher sensitivity.

Figure 6:
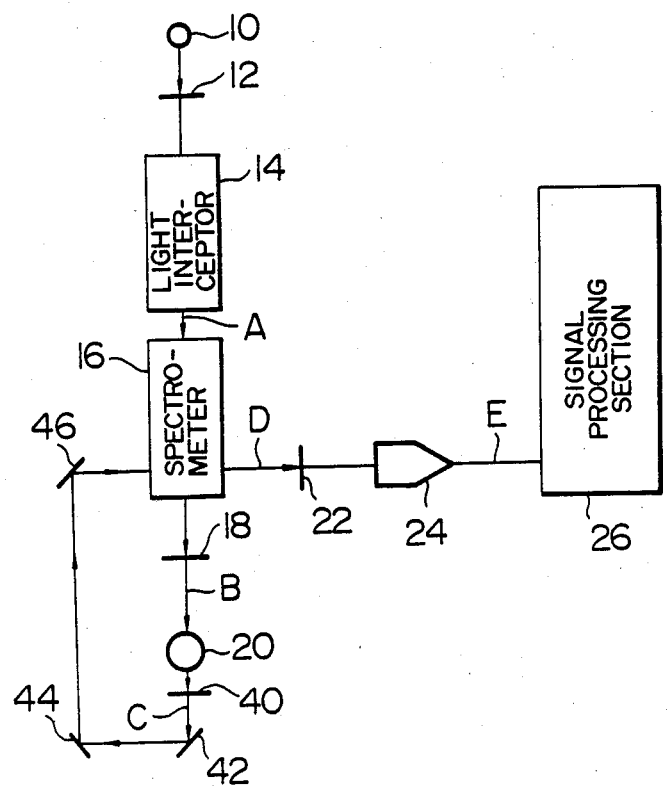
FIGS. 6 and 7 show configurations of the spectrophosphorimeter according to other embodiments of the present invention.
Figure 7:
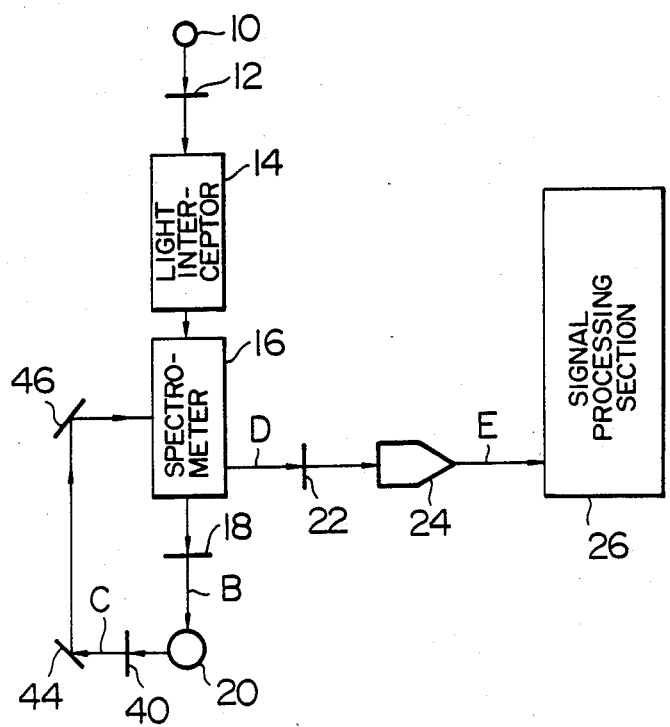

Other embodiments of the present invention are shown in FIGS. 6 and 7, in which the phosphorescence is recovered in different ways. Instead of recovering the phosphorescence from the direction of entry of the excitation light as in the embodiment shown in FIG. 1, the phosphorescence may be picked up with equal effect from the direction identical (FIG. 6) or perpendicular (FIG. 7) to the irradiation of the excitation light as shown in FIGS. 6 and 7 by use of a convergence section 40 and mirrors 42, 44 as shown in FIGS. 6 and 7.

We claim:

1. A spectrophosphorimeter comprising:
   a light source;
   a spectrometer for reducing light from said light source to a spectrum for irradiation on a sample as an excitation light;
   a light intercepter for interrupting the light to be introduced from said light source to said spectrometer;
   means for introducing phosphorescence from said sample into said spectrometer when the light from said light source is interrupted by said light intercepter;
   a detector for detecting at least one spectral component into which said phosphorescence from said sample is separated by said spectrometer and for converting the detected at least one spectral component into an electrical signal; and
   signal processing mens for processing the electrical signal from said detector.

2. A spectrophosphorimeter according to claim 1, wherein said spectrometer includes a concave diffraction grating, a light-source side slit arranged between said concave diffraction grating and said light intercepter, and a sample-side slit interposed between said concave diffraction grating and said sample.

3. A spectrophosphorimeter according to claim 2, wherein said concave diffraction grating is disposed rotatably.

4. A spectrophosphorimeter according to claim 3, further comprising a detection-side slit interposed between said concave diffraction grating and said detector, said detection-side slit and said detector being rotatable around said concave diffraction grating.

5. A spectrophosphorimeter according to claim 2, where said detector includes a plurality of detector elements capable of measuring a spectral distribution.

6. A spectrophosphorimeter according to claim 2, wherein said concave diffraction grating is fixedly disposed, and a detection-side slit is arranged between said concave diffraction grating and said detector.

7. A spectrophosphorimeter according to claim 1, wherein the phosphorescence emitted from said sample is recovered from the side irradiating said sample with the excitation light.

8. A spectrophosphorimeter according to claim 1, wherein the phosphorescence emitted from said sample is recovered from the same direction as that of irradiation of said excitation light on said sample.

9. A spectrophosphorimeter according to claim 1, wherein the phosphoresence emitted from said sample is recovered from the direction perpendicular to the direction of irradiation of the excitation light on said sample.

10. A spectrophosphorimeter according to claim 1, wherein said spectrometer is a single spectrometer and said sample emits said phosphorescence upon irradiation by said excitation light from said spectrometer.

* * * * *